US009675601B2

United States Patent
Gębicki et al.

(10) Patent No.: US 9,675,601 B2
(45) Date of Patent: *Jun. 13, 2017

(54) USE OF QUATERNARY PYRIDINIUM SALTS AS VASOPROTECTIVE AGENTS

(71) Applicant: Pharmena Spólka Akcyjna (Pharmena S.A.), Lódz (PL)

(72) Inventors: Jerzy Gębicki, Lódz (PL); Stefan Chłopicki, Cracow (PL)

(73) Assignee: Pharmena Spólka Akcyjna (Pharmena S.A.), Lodz (PL)

( * ) Notice: Subject to any disclaimer, the term of this patent is extended or adjusted under 35 U.S.C. 154(b) by 0 days.

This patent is subject to a terminal disclaimer.

(21) Appl. No.: 15/146,485

(22) Filed: May 4, 2016

(65) Prior Publication Data

US 2016/0346265 A1    Dec. 1, 2016

Related U.S. Application Data

(60) Continuation of application No. 14/598,888, filed on Jan. 16, 2015, now Pat. No. 9,333,196, which is a division of application No. 13/083,106, filed on Apr. 8, 2011, now Pat. No. 8,969,391, which is a continuation of application No. 10/585,892, filed as application No. PCT/EP2005/050057 on Jan. 7, 2005, now Pat. No. 7,935,717.

(30) Foreign Application Priority Data

Jan. 12, 2004 (PL) ........................ 364348

(51) Int. Cl.
| | |
|---|---|
| A61K 9/00 | (2006.01) |
| A61K 31/455 | (2006.01) |
| A61K 31/4406 | (2006.01) |
| A61K 31/4425 | (2006.01) |
| A23L 33/00 | (2016.01) |

(52) U.S. Cl.
CPC ............ A61K 31/455 (2013.01); A23L 33/30 (2016.08); A61K 9/007 (2013.01); A61K 9/0053 (2013.01); A61K 31/4406 (2013.01); A61K 31/4425 (2013.01)

(58) Field of Classification Search
None
See application file for complete search history.

(56) References Cited

U.S. PATENT DOCUMENTS

| | | | |
|---|---|---|---|
| 5,260,305 A | 11/1993 | Dennick | |
| 6,090,830 A | 7/2000 | Myers et al. | |
| 6,129,930 A | 10/2000 | Bova | |
| 6,406,715 B1 | 6/2002 | Cefali | |
| 6,469,035 B1 | 10/2002 | Cefali | |
| 6,676,967 B1 | 1/2004 | Cefali et al. | |
| 6,746,691 B2 | 6/2004 | Cefali | |
| 6,818,229 B1 | 11/2004 | Cefali et al. | |
| 7,011,848 B1 | 3/2006 | Bova | |
| 7,153,870 B2 | 12/2006 | Mathias | |
| 7,935,717 B2 | 5/2011 | Gebicki et al. | |
| 8,124,631 B2 | 2/2012 | Gebicki et al. | |
| 8,969,391 B2 | 3/2015 | Gebicki et al. | |
| 9,333,196 B2 | 5/2016 | Gebicki et al. | |
| 2001/0014338 A1 | 8/2001 | Cefali | |
| 2003/0157153 A1 | 8/2003 | Cefali | |
| 2003/0161880 A1 | 8/2003 | Cefali | |

(Continued)

FOREIGN PATENT DOCUMENTS

| | | |
|---|---|---|
| DE | 840 698 C | 6/1952 |
| GB | 675 430 | 7/1952 |

(Continued)

OTHER PUBLICATIONS

"Structure and Function of the Water-Soluble Vitamins," in *Harper's Biochemistry: a Lange Medical Book*, 22nd Edition, pp. 549-551, Murray, R.K., et al. (Eds.), Appleton & Lange, Norwalk, CT, United States (1990).

Bartuś, M., et al., "1-Methylnicotinamide (MNA) prevents endothelial dysfunction in hypertriglyceridemic and diabetic rats," *Pharmacol Rep.* 60:127-138, Institute of Pharamacology Polish Academy of Sciences, Poland (Jan.-Feb. 2008).

Bodor, E.T., and Offermanns, S., "Nicotinic acid: an old drug with a promising future," *Br. J. Pharmacol.* 153:S68-S75, Nature Publishing Group, England (Mar. 2008).

Carlson, L.A., et al., "A case of massive hypertriglyceridemia corrected by nicotinic acid or nicotinamide therapy," *Atherosclerosis* 16(3):359-368, Elsevier, Ireland (Nov.-Dec. 1972).

(Continued)

*Primary Examiner* — Matthew Coughlin
*Assistant Examiner* — Po-Chih Chen
(74) *Attorney, Agent, or Firm* — Sterne, Kessler, Goldstein & Fox P.L.L.C.

(57) ABSTRACT

The invention relates to the use of quaternary pyridinium salts of formula (I),

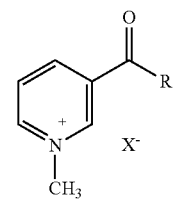

wherein R is $NH_2$, $CH_3$, or $N(H)CH_2OH$ group, and X is pharmaceutically acceptable counterion, for the preparation of vasoprotective agent for the treatment or prevention of conditions or diseases associated with dysfunction of vascular endothelium, oxidative stress, and/or insufficient production of endothelial prostacyclin $PGI_2$, in particular but not exclusively if the above coincides with hypercholesterolemia, hypertriglyceridemia or low HDL level.

15 Claims, 7 Drawing Sheets

(56) References Cited

U.S. PATENT DOCUMENTS

| | | | |
|---|---|---|---|
| 2004/0132737 | A1 | 7/2004 | Cormier et al. |
| 2005/0130990 | A1 | 6/2005 | Cormier et al. |
| 2005/0255158 | A1 | 11/2005 | Bova |
| 2006/0263428 | A1 | 11/2006 | Cefali |
| 2007/0021379 | A1 | 1/2007 | Bender et al. |
| 2007/0249622 | A1 | 10/2007 | Cormier et al. |
| 2008/0207702 | A1 | 8/2008 | Gebicki et al. |
| 2008/0221085 | A1 | 9/2008 | Cormier et al. |
| 2008/0221172 | A1 | 9/2008 | Marcinek et al. |
| 2008/0227831 | A1 | 9/2008 | Bender et al. |
| 2014/0296305 | A1 | 10/2014 | Gebicki et al. |
| 2015/0133508 | A1 | 5/2015 | Gebicki et al. |

FOREIGN PATENT DOCUMENTS

| | | | |
|---|---|---|---|
| WO | WO 99/06046 | A1 | 2/1999 |
| WO | WO 00/40559 | A1 | 7/2000 |
| WO | WO 2005/067927 | A2 | 7/2005 |
| WO | WO 2006/052569 | A1 | 5/2006 |

OTHER PUBLICATIONS

Carlson, L.A., et al., "Nicotinic acid: the broad-spectrum lipid drug. A 50th anniversary review," *J. Intern. Med.* 258:94-114, Blackwell Publishing Ltd., England (Aug. 2005).

Dalton, C., et al., "Relationship of Nicotinamide and Nicotinic Acid to Hypolipidemia," *Biochem. Pharma.* 19:2609-2619, Pergamon Press, England (Jul. 1970).

Filetti, S., et al., "Insulin receptor down-regulation, prevention at a post-receptor site," *Endocrinology* 108(6):2409-11, Endocrine Society, United States (Jun. 1981).

Fischer, L.J., et al., "Characteristics of nicotinamide and N1-methylnicotinamide protection from alloxan diabetes in mice," *Toxicol. Appl. Pharmacol.* 70(1):148-55, Academic Press, United States (Aug. 1983).

Fukushima, T., et al., "Possible role of 1-methylnicotinamide in the pathogenesis of Parkinson's disease," *Exp. Toxicol. Pathol.* 53(6):469-73, Urban and Fischer, Germany (Feb. 2002).

Fukushima, T., et al., "Radical formation site of cerebral complex I and Parkinson's disease," *J. Neurosci. Res.* 42(3):385-90, Wiley Interscience, United States (Oct. 1995).

Fung, M.A. and Frohlich, J.J., "Common problems in the management of hypertriglyceridemia," *CMAJ* 167(11):1261-6, Canadian Medical Association, Canada (Nov. 2002).

Gebicki, J., et al., "1-Methylnicotinamide: a potent anti-inflammatory agent of vitamin origin," *Pol. J. Pharmacol.* 55(1):109-112, Polish Academy of Sciences, Institute of Pharmacology, Poland (Jan.-Feb. 2003).

GLOBinMED, "Trigonella foenum-graecum", Global Infomation Hub on Integrated Medicine, accessed at http://210.19.20.8/NHIContent/safetyDetail.aspx?id-SAF00013, Malaysia, Jul. 8, 2007 (XPOO2445860).

Jaconello, P., Mattiussi, A., Blais, D., "Niacin versus niacinamide," *Can. Med. Assoc. J.* 147:990, CMA, Canada (Oct. 1992).

Lea, M.A., et al., "Effects of nicotinamide and structural analogs on DNA synthesis and cellular replication of rat hepatoma cells," *Cancer Biochem. Biophys.* 7(3):195-202, Gordon and Breach Science Publishers, England (Sep. 1984).

Oettgen, H.F., et al., "Effects of nicotinamide and related compounds on the antileukemic activity of 2-amino-1,3,4-thiadiazole," *Cancer Res.* 20:1597-1601, American Association for Cancer Research, United States (Dec. 1960).

Patani, G.A. and LaVoie, E.J., "Bioisosterism: A Rational Approach in Drug Design," *Chem Rev.* 96(8):3147-3176, American Chemical Society, United States (Dec. 1996).

Pike, Nicholas B., "Flushing out the role of GPR109A (HM74A) in the clinical efficacy of nicotinic acid," The *J. of Clin. Invest.*, 115:3400-3403, American Society for Clinical Investigation, United States (Dec. 2005).

Shibata, K. and Matsuo, H., "Correlation between niacin equivalent intake and urinary excretion of its metabolites, N'-methylnicotinamide, N'-methyl-2-pyridone-5-carboxamide, and N'-methyl-4-pyridone-3-carboxamide, in humans consuming a self-selected food," *Am. J. Clin. Nutr.* 50(1):114-9, American Society of Clinical Nutrition, United States (Jul. 1989).

Taguchi, H., "Vitamins and apoptosis—Induction of apoptosis in human cancer cells by nicotinic acid-related compounds," *Nippon Rinsho.* 57(10):2319-2324, Nippon Rinsho Co., Japan (Oct. 1999) (Abstract Only).

Wagner, A.M., et al., "Apolipoprotein(B) identifies dyslipidemic phenotypes associated with cardiovascular risk in normocholesterolemic type 2 diabetic patients," *Diabetes Care* 22(5):812-7, American Diabetes Association, USA (May 1999).

Walter, Anthony A.J., "Megavitamin and megamineral therapy in childhood," *Can. Med. Assoc. J.* 146:2140, CMA, Canada (Jun. 1992).

Wise, A., et al., "Molecular Identification of High and Low Affinity Receptors for Nicotinic Acid," *J. Biol. Chem.* 278(11):9868-9874, The American Society for Biochemistry and Molecular Biology, Inc., United States (Mar. 2003).

Partial English language translation of German Patent Publication No. DE 840 698, p. 1, lines 1-24,1952.

International Search Report for Application No. PCT/EP2005/050057, European Patent Office, Netherlands, dated Sep. 30, 2005.

Harper's Biochemistry, Twenty-second Edition, R.K. Murray, et al., eds., Appleton & Lange, Norwalk, CT, 1990, pp. 549-551.

"Trigonella foenum-graecum", XP002445860 (2007).

Lanham et al., "Prostacyclin deficiency in a young woman with recurrent thrombosis," *The British Medical Journal* 292:435-436 (1986).

USE OF QUATERNARY PYRIDINIUM SALTS AS VASOPROTECTIVE AGENTS

The present invention relates to the use of certain quaternary pyridinium salts for the preparation of a vasoprotective agent for the treatment and/or prevention of conditions or diseases associated with dysfunction of vascular endothelium, oxidative stress, and/or insufficient production of endothelial prostacyclin (PGI2), in particular but not exclusively if the above coincides with hypercholesterolemia/hypertriglyceridemia, as well as the use of pyridinium salts for oral use in diet supplementation.

There is increasing evidence that endothelial dysfunction plays a key role in the formation and progression of atherosclerotic plaque. Endothelial dysfunction has recently gained diagnostic, prognostic and therapeutic significance in atherothrombosis (Heitzer T, Schlinzig T, Krohn K, Meinertz T, Munzel T. Endothelial dysfunction, oxidative stress, and risk of cardiovascular events in patients with coronary artery disease. *Circulation* 2001; 104:2673-2678; Schachinger V, Britten M B, Zeiher A M. Prognostic impact of coronary vasodilator dysfunction on adverse long-term outcome of coronary heart disease. *Circulation* 2000; 101: 1899-1906; Perticone F, Ceravolo R, Pujia A, Ventura G, Iacopino S, Scozzafava A, Ferraro A, Chello M, Mastroroberto P, Verdecchia P, Schillaci G. Prognostic significance of endothelial dysfunction in hypertensive patients. *Circulation* 2001; 104:191-196; Suwaidi J A, Hamasaki S, Higano S T, Nishimura R A, Holmes D R, Jr., Lerman A. Long-term follow-up of patients with mild coronary artery disease and endothelial dysfunction. *Circulation* 2000; 101:948-954). Clinically, endothelial dysfunction is identified as impairment of biological activity of NO, which is diagnosed as an impairment of vasodilating NO activity. Impairment of NO activity coincides with oxidant stress (Heitzer T, Schlinzig T, Krohn K, Meinertz T, Munzel T. Endothelial dysfunction, oxidative stress, and risk of cardiovascular events in patients with coronary artery disease. *Circulation* 2001; 104:2673-2678) and impairment of PGI2 synthesis (Kyrle P A, Minar E, Brenner B, Eichler H G, Heistinger M, Marosi L, Lechner K. Thromboxane $A_2$ and prostacyclin generation in the microvasculature of patients with atherosclerosis—effect of low-dose aspirin. *Thromb Haemost* 1989; 61:374-377), although systemic level of $PGI_2$ may be elevated. Indeed, several years ago it was proposed that increased lipid peroxidation might promote development of atherosclerosis owing to selective impairment of prostacyclin synthesis in endothelial cells and subsequent activation of platelets (Gryglewski R J. Prostacyclin and atherosclerosis. TIPS 1980; 1:164-1.68; Gryglewski R J. Prostaglandins, platelets, and atherosclerosis. *CRC Crit Rev Biochem* 1980; 7:291-338; Gryglewski R J, Szczeklik A. Prostacyclin and atherosclerosis—experimental and clinical approach. 1983; 213-226). This concept was then supported experimentally. It is apparent now that impairment of PGI2 synthesis in endothelium may lead to the excessive stimulation of TP receptors in endothelium and vascular smooth muscle cells by $TXA_2$, PGH2 or other eicosanoids, and to subsequent vasoconstriction, platelet aggregation, and inflammatory response of endothelium as well as endothelial apoptosis (Chlopicki S, Gryglewski R J. Endothelial secretory function and atherothrombosis in "The Eicosanoids", chapter 23, 267-276. ed. P. Curtis-Prior, John Wiley and Sons, Ltd, 2004). This means that deficiency of $PGI_2$ may trigger or enhance inflammatory and thrombotic processes in vascular wall, which are now considered to be the key elements of atherosclerosis.

It has been accepted that elevated low-density lipoprotein cholesterol (LDL) and/or triglyceride (TG) plasma levels represent major risk factors for the development of atherosclerosis (Levine G N, Keaney J F Jr, Vita J A. Cholesterol reduction in cardiovascular disease. Clinical benefits and possible mechanisms. *N Engl J Med* 1995; 332:512-521). Moreover, a low plasma level of high-density lipoprotein cholesterol (HDL) is an important independent risk factor of atherosclerosis. HDL has the potential ability to prevent and correct endothelial dysfunction by increasing availability of NO and $PGI_2$. (Ng DS. Treating low HDL—from bench to bedside. *Clin Biochem* 2004; 37:649-659; Chapman M J, Assman G, Fruchart J C, Shepherd J, Sirtoti C. Raising high-density lipoprotein cholesterol with reduction of cardiovascular risk: the role of nicotinic acid—a position paper developed by the European Consensus Panel on HDL-C. *Curr Med Res Opin* 2004; 20:1253-1268; Calabresi L, Gomarashi M, Franceschini G. Endothelial protection by high-density lipoproteins. *Arterioscler Thromb Vasc Biol* 2003; 290:2292-2300).

In WO00/40559 therapeutic and cosmetic uses of certain nicotinamide derivatives, 1,3-disubstituted pyridinium salts, including 1-methylnicotinamide ($MNA^+$) and 1-methyl-N'-(hydroxymethyl)nicotinamide ($MNAF^+$) salts were disclosed. It was reported that said derivatives have the utility in topical treatment of skin diseases, in particular crural ulceration, acne, psoriasis, atopic dermatitis, vitiligo, as well as burns and scalds and in wound healing. Said derivatives have also the activity of promoting hair re-growth, therefore they are useful in the treatment of hair loss of different origin. Different types of topical formulations for administration of these compounds on the skin or mucosal surface are described, like shampoo, ointments, creams, gels, lotions, solutions, aerosols, etc., and for oral administration in the treatment of skin diseases. Also, cosmetic action of these compounds was described, in particular regenerating and smoothing of the skin.

Effects of 1-methylnicotinamide chloride ($MNA^+$) in some skin diseases were described in a recent publication (G ę bicki J, Sysa-Ję drzejowska A, Adamus J, Woźniacka A, Rybak M, Zielonka J. 1-Methylnicotinamide: a potent anti-inflammatory agent of vitamin origin. *Pol J Pharmacol* 2003; 55:109-112). It has been proposed that $MNA^+$ displays anti-inflammatory action, though the mechanism of this effect was not elucidated.

1-Methyl-3-acetylpyridinium salt ($MAP^+$), was described in a publication (Takashi Sakurai, Haruo Hosoya. Charge transfer complexes of nicotinamide-adenine dinucleotide analogs and flavine mononucleotide. *Biochim. Biophys. Acta* 1966; 112(3):359-468).

Now it has been found that $MAP^+$ and some of the compounds described in WO00/40559, in particular $MNA^+$ and $MNAF^+$ possess unique pharmacological properties associated with their ability to release endogenous prostacyclin (PGI2) from vascular endothelium, which property distinguishes them from closely structurally related nicotinamide, nicotinic acid, trigonelline and endogenous $MNA^+$ metabolites, such as 1-methyl-2-pyridone-5-carboxyamide (2-PYR) and 1-methyl-4-pyridone-3-carboxyamide (4-PYR). Surprisingly, as found by the present inventors, certain compounds are endowed with the ability to correct the lipoprotein profile, in particular to lower LDL and/or TG plasma level and to raise HDL plasma level, leading to anti-atherosclerotic effects. Independently of the effect of certain quaternary pyridinium salts of the invention on lipoprotein profile, augmentation of $PGI_2$ synthesis by quaternary pyridinium salts found by the present inventors may show therapeutic potential in many diseases as discussed below, where endothelial dysfunction, oxidant stress, and/or $PGI_2$ deficiency play a pathogenetic role, including those associated with hypercholesterolemia/hypertriglyceridemia.

Figure 1:
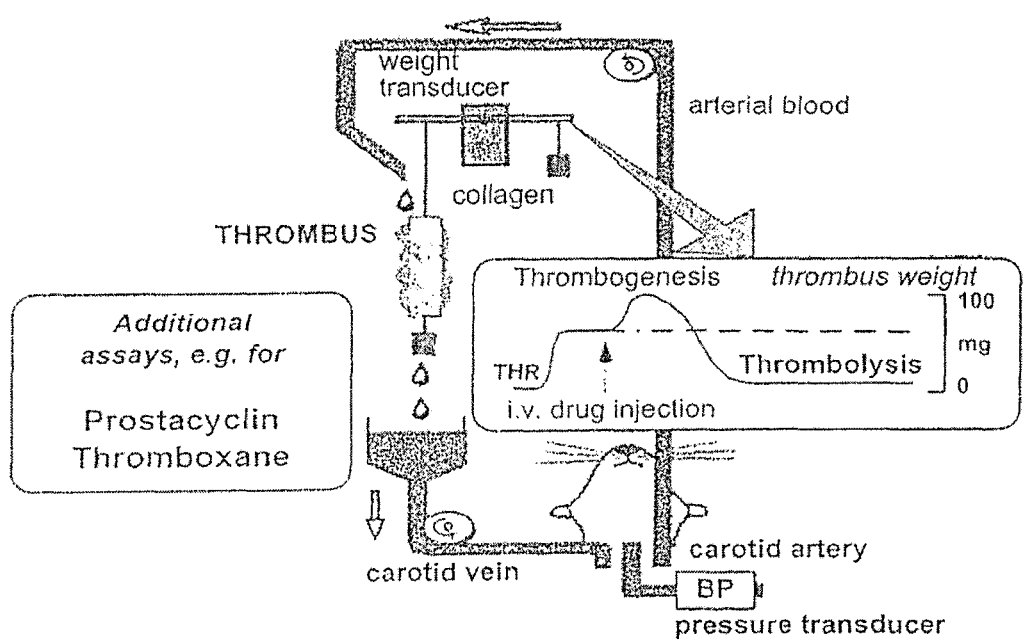
FIG. 1 Scheme of the method for detection of thrombolytic action of drugs in vivo in rats (according to Gryglewski)

The present invention provides in its first aspect the use of quaternary pyridinium salts of the formula I:

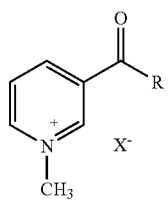

I wherein R is $NH_2$, $CH_3$, or $N(H)CH_2OH$ group, and X is pharmaceutically acceptable counterion, for the preparation of vasoprotective agent for the treatment or prevention of conditions or diseases associated with dysfunction of vascular endothelium, oxidative stress, and/or insufficient production of endothelial prostacyclin $PGI_2$.

Preferably, said dysfunction of vascular endothelium, oxidative stress, and/or insufficient production of endothelial prostacyclin $PGI_2$ is associated with hypercholesterolemia, hypertriglyceridemia or low HDL level.

Particularly advantageous activity of the compounds of the formula I is their endothelial action associated with release of $PGI_2$, due to which said compounds of formula I may improve perfusion in tissues, exert anti-aggregatory, thrombolytic, anti-apoptotic, anti-atherosclerotic activity, and protect gastrointestinal mucosa.

The advantage of the invention is that thrombolytic action of the compounds of the formula I is not accompanied by hypotensive activity.

In one embodiment of the invention, said condition or disease is atherosclerosis of vascular bed of any kind, including chronic coronary disease, ischemic cerebrovascular episode or artherosclerosis of the extremities, including thromboangiitis obliterans.

In another embodiment said condition or the disease is acute cardiovascular event associated with atherosclerosis, in particular sudden cardiac death, acute coronary syndrome (including unstable coronary artery disease, myocardial infarct), the necessity of coronary angioplasty (PCI), coronary-aortal by-pass surgery (CABG), ischemic stroke, or peripheral circulation revascularization.

In yet another embodiment said condition or disease is selected from the group of risk factors for atherosclerosis, comprising the following: hypercholesterolemia, arterial hypertension, smoking, hyperhomocysteinaemia, insulin resistance, diabetes, menopause, aging, obesity, mental stress, infections, inflammatory states, including periodontal diseases, reumathoid arthritis, allograft vasculopathy or nitrate tolerance.

In yet another embodiment said condition or the disease is dyslipidemia; in particular hypercholesterolemia or hypertriglyceridemia in particular associated with low plasma level of HDL.

In yet another embodiment said condition or disease is thrombosis that is not related directly with atherosclerosis, in particular thrombosis associated with implantation of metallic vascular prostheses (stents), coronary-aortal by-pass surgery (CABG), any type of surgery with extracorporeal circulation, hemodialysis, venous thrombo-embolic disease.

In further embodiment said condition or disease is selected from the following group: chronic heart failure, pulmonary hypertension, microvascular diabetic complications, like diabetic retinopathy and nephropathy, diabetic neuropathy, nephrotic syndrome, chronic renal failure, adults respiratory distress syndrome (ARDS), cystic fibrosis, chronic obstructive pulmonary disease (COPD), preeclampsia/eclampsia, erectile dysfunction, Stein-Leventhal syndrome, sleep apnea, systemic lupus erythematosus, sickle cell anemia, non-specific inflammatory bowel diseases, gastric or duodenal ulcers, glaucoma, chronic liver disease, primary amyloidosis, neurodegenerative diseases, in particular neurodegenerative disease selected from vascular dementia, Alzheimer's disease and Parkinson's disease.

Also advantageous is the use of the compounds of formula I for the preparation of a medicament for prophylaxis or treatment of gastric or duodenal ulcer.

In a further preferred embodiment said condition or disease is chronic liver disease, in particular chronic viral hepatitis.

In a further preferred embodiment said condition or disease is chronic obstructive pulmonary disease (COPD).

Said medicament may be in a form suitable for any administration route, such as oral, parenteral, intranasal or inhalation route. Such route of administration will depend of course on the particular state or disease being treated.

In case of a medicament intended for the treatment of chronic obstructive pulmonary disease (COPD) it will preferably be presented in the form suitable for inhaled administration via the inhalation route.

As defined above, X– may be any physiologically acceptable counterion. Thus, salts of the formula I may be derived from any physiologically acceptable acid, both organic and inorganic. Suitable salts with inorganic acids are for example chloride, bromide, iodide and carbonate; suitable salts with organic acids may be salts with mono-, di- and tricarboxylic acids, for example acetate, benzoate, salicylate, hydroxyacetate, lactate, malonate and citrate. Preferred salts are chlorides, benzoates, salicylates, acetates, citrates and lactates; especially advantageous are chlorides.

Specific compounds of the formula (I) are 1-methylnicotinamide salts (MNA$^+$), 1-methyl-3-acetylpyridinium salts (MAP$^+$) and 1-methyl-N'-(hydroxymethyl)nicotinamide salts (MNAF$^+$).

The invention in the second aspect provides a method of treatment and/or prevention of conditions or diseases associated with dysfunction of vascular endothelium, oxidative stress, and/or insufficient production of endothelial PGI$_2$ (associated or not with hypercholesterolemia, hypertriglyceridemia or low HDL level), in particular such as discussed above, comprising administration to a subject in a need of such treatment a therapeutically effective amount of a quaternary pyridinium salt of formula I as defined above In one embodiment of the method of treatment according to the invention said condition or the disease is atherosclerosis of vascular bed of any kind, including chronic coronary disease, ischemic cerebrovascular episode or artherosclerosis of the extremities, including thromboangigitis obliterans.

In another embodiment of the method of treatment according to the invention the said condition or disease is acute cardiovascular event associated with atherosclerosis, in particular sudden cardiac death, acute coronary syndrome (including unstable coronary artery disease, myocardial infarct), the necessity of coronary angioplasty (PCI), coronary-aortal by-pass surgery (CABG), ischemic stroke, or peripheral circulation revascularization.

In yet another embodiment of the method of treatment according to the invention said condition or disease is selected from the group of risk factors for atherosclerosis, comprising the following: hypercholesterolemia, arterial hypertension, smoking, hyperhomocysteinaemia, insulin resistance, diabetes, menopause, aging, obesity, mental stress, infections, inflammatory states, including periodontal diseases, reumathoid arthritis, allograft vasculopathy or nitrate tolerance.

In yet another embodiment of the method of treatment according to the invention said condition or the disease is dyslipidemia, in particular hypercholesterolemia or hypertriglyceridemia, in particular associated with low plasma level of HDL.

In yet another embodiment of the method of treatment according to the invention said condition or disease is thrombosis that is not related directly with atherosclerosis, in particular thrombosis associated with implantation of metallic vascular prostheses (stents), coronary-aortal by-pass surgery(CABG), any type of surgery with extracorporeal circulation, hemodialysis, venous thrombo-embolic disease.

In a further embodiment of the method of treatment according to the invention said condition or disease is selected from the following group: chronic heart failure, pulmonary hypertension, microvascular diabetic complications, like diabetic retinopathy and nephropathy, diabetic neuropathy, nephrotic syndrome, chronic renal failure, adults respiratory distress syndrome (ARDS), cystic fibrosis, chronic obstructive pulmonary disease (COPD), preeclampsia/eclampsia, erectile dysfunction, Stein-Leventhal syndrome, sleep apnea, systemic lupus erythematosus, sickle cell anemia, non-specific inflammatory bowel diseases, gastric or duodenal ulcers, glaucoma, chronic liver disease, primary amyloidosis, neurodegenerative diseases, in particular neurodegenerative disease selected from vascular dementia, Alzheimer's disease and Parkinson's disease.

In a further preferred embodiment said condition or disease is chronic liver disease, in particular chronic viral hepatitis.

In a further preferred embodiment said condition or disease is chronic obstructive pulmonary disease (COPD).

Also advantageous is the use of the compounds of formula I in the method of prophylaxis or treatment of gastric or duodenal ulcer.

Quaternary pyridinium salts of formula I may be administered alone or in combination with other cardiovascular agent.

Pyridinium salts of formula I may be administered in particular orally, in the form of conventional oral preparations, such as tablets, capsules, oral solutions/suspensions in pharmaceutically acceptable liquid carrier. Said formulations may be prepared using conventional methods known in the art and include conventional pharmaceutical excipients and carriers.

Pyridinium salts of formula I may be also administered parenterally, in the form of injections, including subcutaneous and intravenous injections and infusions.

Other contemplated routes of administration are by inhalation, intranasally and rectally.

In any case the route of administration will of course depend on the particular disease being treated.

For example, in case of a treatment of chronic obstructive pulmonary disease (COPD) pyridinium salts it will preferably be administered in the form suitable for inhaled administration via the inhalation route.

Daily dose of the pyridinium salts of the formula I may be in the range of 10 to 1000 mg and may be administered in single or divided doses.

The present invention relates also to a method for enhancing a prostacyclin levels in mammals, which comprises oral administration of effective amount of quaternary pyridinium salt of formula I as defined above.

The present invention provides also quaternary pyridinium salts of formula I as defined above, for use in oral diet supplementation. Pyridinium salts of formula I, when used as an oral diet supplement, enhance the prostacyclin level, thereby acting as vasoprotective agents.

The present invention provides further a use of pyridinium salts of the formula I as defined above, for the preparation of nutritional preparation for vascular protection in mammals in states or diseases associated with dysfunction of vascular endothelium, oxidative stress, and/or insufficient production of endothelial prostacyclin (PGI$_2$), in particular associated with hypercholesterolemia, hypertriglyceridemia or low HDL level.

Said condition or disease wherein nutritional preparation may be administered is atherosclerosis, especially in patients with chronic coronary disease, ischemic cerebrovascular episode or artherosclerosis of the extremities, including thromboangigitis obliterans.

Said condition or disease wherein nutritional preparation may be administered may be also selected from the group of risk factors for atherosclerosis, comprising the following: hypercholesterolemia, arterial hypertension, smoking, hyperhomocysteinaemia, insulin resistance, diabetes, menopause, aging, obesity, mental stress, infections, inflammatory states, including periodontal diseases, reumathoid arthritis, allograft vasculopathy or nitrate tolerance.

Said condition or disease wherein nutritional preparation may be administered is dyslipidemia, in particular hypercholesterolemia, hypertriglyceridemia in particular associated with low plasma level of HDL.

Said condition or disease wherein nutritional preparation may be administered may be also thrombosis that is not related directly with atherosclerosis, in particular thrombosis associated with implantation of metallic vascular prostheses (stents), coronary-aortal by-pass surgery (CABG), any type of surgery with extracorporeal circulation, hemodialysis, venous thrombo-embolic disease.

Specific pyridinium salts for use in diet supplementation and/or as nutritional preparation are compounds of the formula (I), wherein R is $CH_3$ group.

Specific pyridinium salts for use in diet supplementation and/or as nutritional preparation are compounds of the formula (I), wherein R is $NH_2$ group.

Specific pyridinium salts for use in diet supplementation and/or as nutritional preparation are compounds of the formula (I), wherein R is $N(H)CH_2OH$ group.

Dietary supplements and nutritional preparations may have the form suitable for oral ingestion, such as tablets, capsules, solutions and suspensions for drinking, and similar, conventional and known in pharmaceutical art and prepared according to techniques known in the art with the use of conventional excipients and carriers.

Advantageously, dietary supplement or nutritional preparation may incorporate at least 5% by weight of the pyridinium salt of the formula I.

The invention is further illustrated by the following Examples, which show pharmacological activity of pyridinium salts.

EXAMPLE I

Thrombolytic Activity

Thrombolytic activity of quaternary pyridinium salts was assessed using original method of Gryglewski et al., (Gryglewski R J, Korbut R, Ocetkiewicz A, Stachura J. In vivo method for quantitation for anti-platelet potency of drugs. *Naunyn Schmiedebergs Arch Pharmacol* 1978; 302:25-30), the scheme of which was shown on FIG. 1.

Wistar rats of body weight 300-350 g were anaesthetised (thiopental 30 mg $kg^{-1}$ i.p.) and heparinised (unfractionated heparin 800 i.u. $kg^{-1}$ i.v.). Arterial blood pressure was measured from cannulated right carotid artery, and extracorporal circulation was established between left carotid artery and left jugular vein. A collagen strip from rabbit tendon of Achilles was superfused with arterial blood in extracorporal circulation at a rate of 1.5 ml $min^{-1}$ and its weight was continuously monitored by an auxotonic Harvard transducer.

During the initial 20-30 mM of superfusion the strip was gaining in weight by 80-120 mg because of deposition of platelet-rich thrombi and then in control conditions stayed unchanged during next 3-5 hrs. Thrombolytic response was detected by a fall in weight of a thrombi. Arterial blood pressure was also monitored, so this model enabled the analysis of thrombolytic and hypotensive action of a compound (FIG. 1).

The analysis of the thrombolytic response in this experimental set-up was complemented by the assay of 6-keto-$PGF_{1\alpha}$, $TXB_2$ and $PGE_2$ in arterial blood plasma. For this purpose blood samples (500 µl) were collected in Eppendorff tubes with indomethacin to yield its final concentration of 10 µM, and EDTA to yield the final concentration of 1 mM. Then, the blood samples were spinned for 5 min at 2.000×g. Plasma samples were stored at −70° C. The prostanoids were assayed using the enzyme immunoassay kits (Cayman Chemical Co, Ann Arbor, Mich.).

Intravenous administration of $MNA^+$ (3-30 mg/kg) produced a concentration-dependent thrombolysis in Wistar rats with extracorporal circulation. A maximum response was observed at the $MNA^+$ dose of 30 mg/kg. Single injection of $MNA^+$ at a dose of 30 mg/kg induced a long-lasting thrombolytic response at the level of 42±4% and remained at approximately the same level for 2-3 hours of the observation period. In contrast to $MNA^+$, nicotinamide, nicotinic acid, trigonelline and 2-PYR (endogenous metabolite of $MNA^+$), each of them at 30 mg/kg, failed to induce a significant thrombolytic response. Nicotinamide and nicotinic acid-induced responses were transient (less then 15-20 minutes) and at their maximum amounted merely to 9±0.6%, 5±0.9%, respectively). Trigonelline did not produce any thrombolytic response and response to 2-PYR was also very weak (<10%) and transient (<15 min). The potency and duration of thrombolytic responses to $MNA^+$, nicotinamide and nicotinic acid correlated with a pattern of 6-keto-$PGF_{1\alpha}$ release to arterial plasma induced by these compounds. $MNA^+$ (30 mg/kg) induced a substantial increase in levels of 6-keto-$PGF_{1\alpha}$ as early as 15 minutes after drug injection (from 104±7 to 460±58 pg/ml) which than reached its plateau of around 400 pg/ml for at least one hour. On the other hand neither $TXB_2$ nor $PGE_2$ levels changed significantly in response to $MNA^+$. Sluggish rise in $TXB_2$ levels was time-dependent and observed also after saline injection. Levels of 6-keto-$PGF_{1\alpha}$ did not increase after injection of nicotinamide or after injection of nicotinic acid (30 mg/kg).

In the presence of indomethacin (5 mg/kg) thrombolytic response to $MNA^+$ was abrogated, similarly as MNA-induced release of 6-keto-$PGF_{1\alpha}$. Importantly, thrombolysis induced by $MNA^+$ (30 mg/kg) was not associated with a fall in arterial blood pressure. Collagen-induced aggregation in platelet-rich plasma in vitro was not affected by $MNA^+$ up to concentration of 10 mM, this excluding the possibility that dissipation of plate-let-rich thrombi in vivo was due to the direct effect of $MNA^+$ on platelets. Furthermore $MNA^+$ (1 mM) did not inhibit latex-induced activation of neutrophils, this suggesting a possible selectivity of $MNA^+$ towards endothelium.

Figure 2:
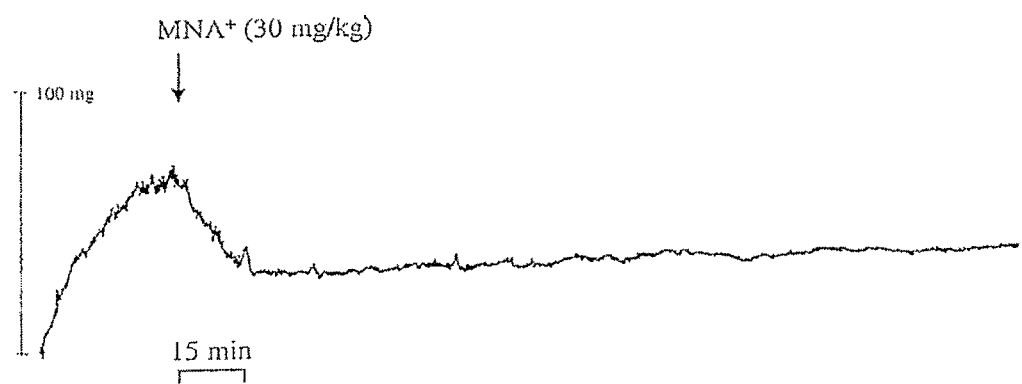
FIG. 2 Thrombolytic response induced by intravenous administration of $MNA^+$ in vivo (30 mg/kg)
Figure 3:
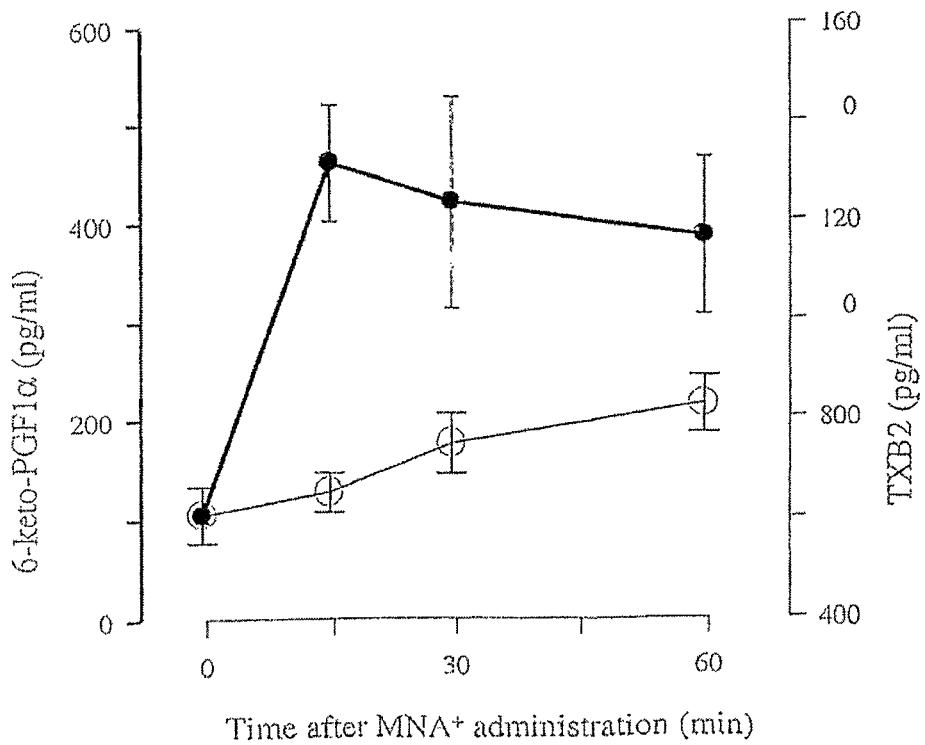
FIG. 3 Changes in plasma levels of 6-keto-$PGF_{1\alpha}$ (●) and $TXB_2$ (○) after intravenous administration of $MNA^+$ (30 mg/kg)
Figure 4:
FIG. 4 Lack of thrombolytic response after intravenous administration of nicotinamide or nicotinic acid (30 mg/kg).
Figure 4:
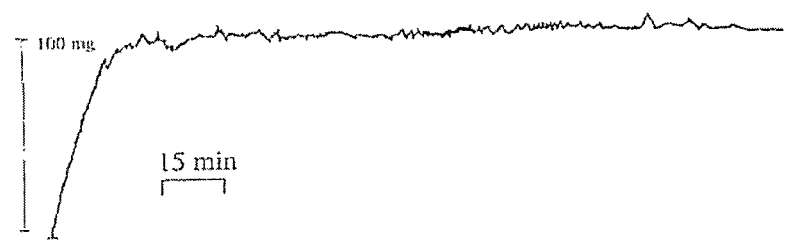
Figure 5:
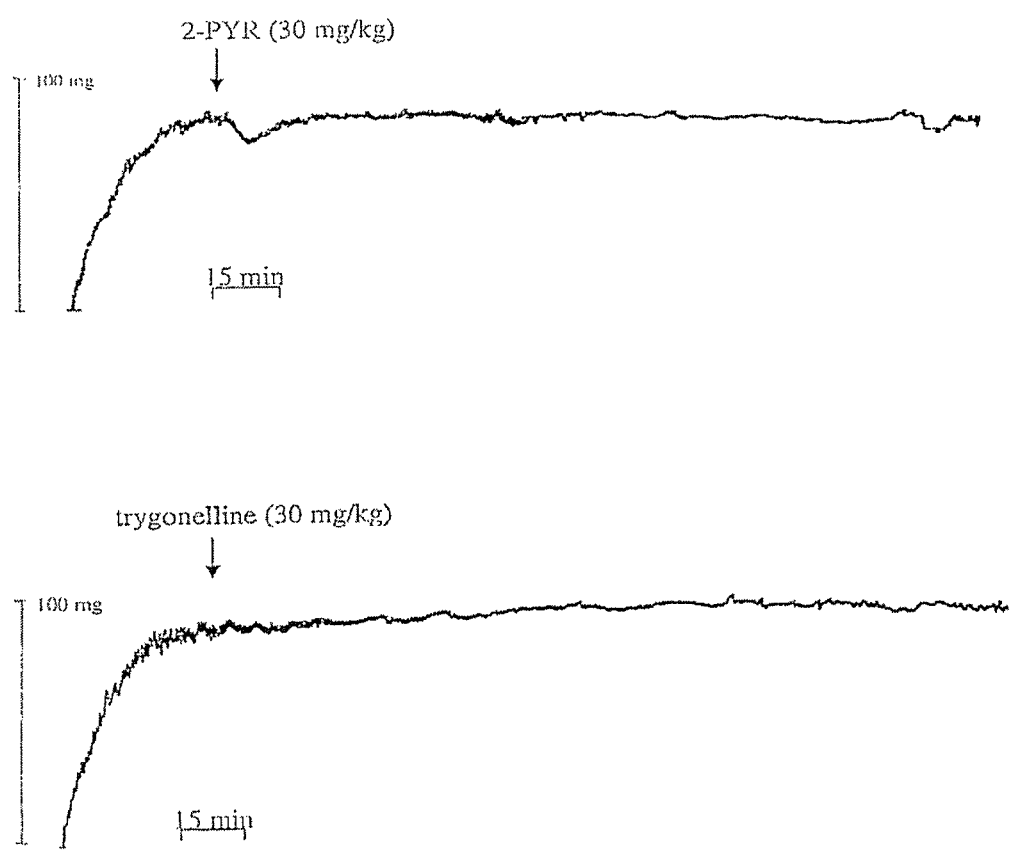
FIG. 5 Lack of thrombolytic response after intravenous administration of 2-PYR or trigonelline (30 mg/kg).
Figure 6:
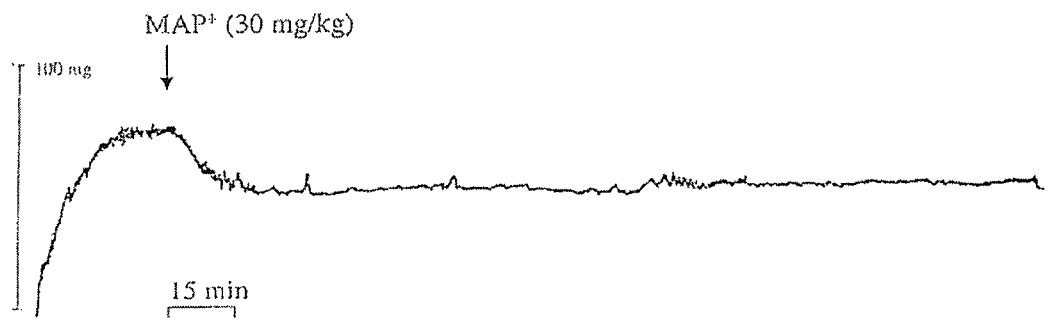
FIG. 6 Thrombolytic response induced by intravenous administration of $MAP^+$ in vivo (30 mg/kg)
Figure 7:
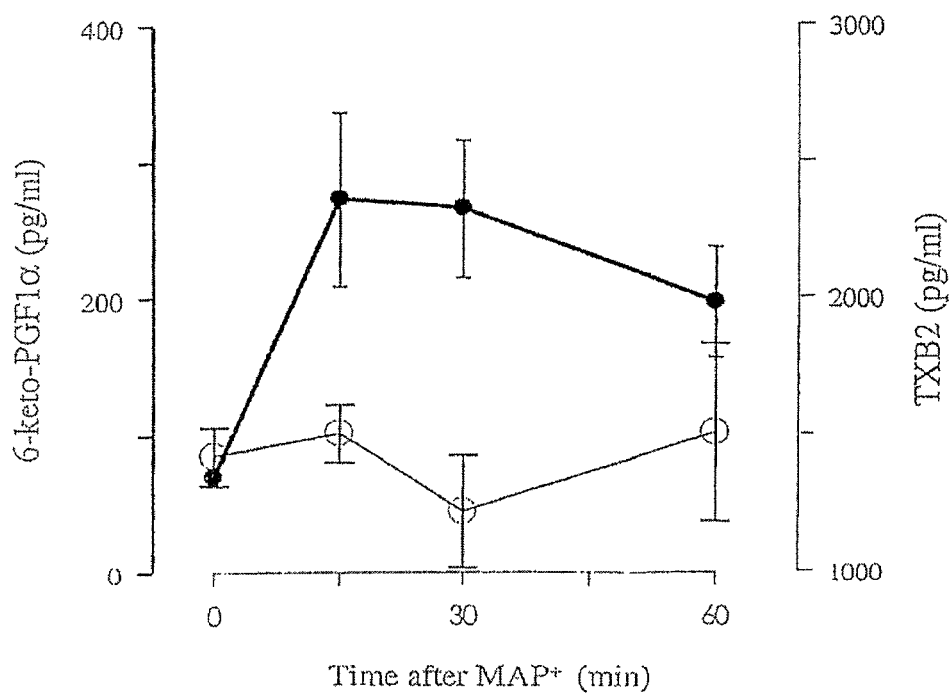
FIG. 7 Changes in plasma levels of 6-keto-$PGF_{1\alpha}$ (●) and $TXB_2$ (○) after intravenous administration of MAP in vivo (30 mg/kg)
Figure 8:
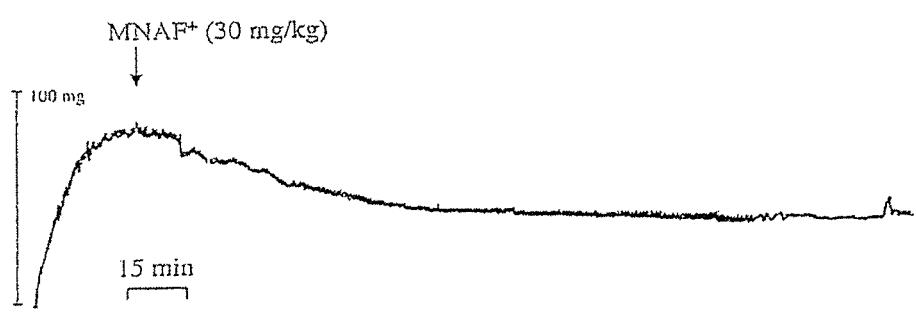
FIG. 8 Thrombolytic response induced by intravenous administration of $MNAF^+$ (30 mg/kg)
Figure 9:
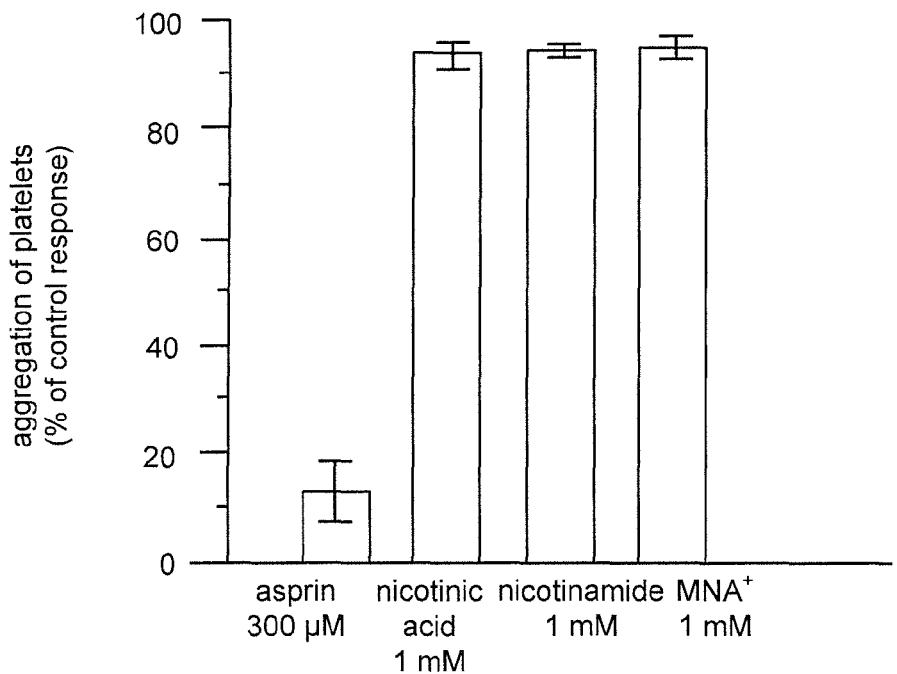
FIG. 9 Lack of effect of $MNA^+$ on collagen-induced aggregation of platelets (1 mg/ml)
Figure 10:
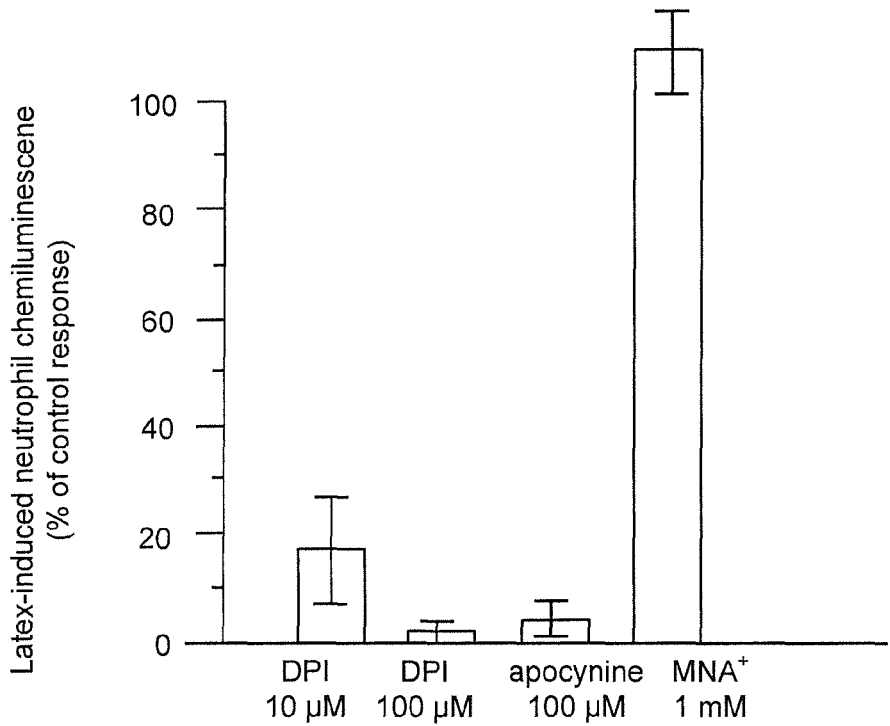
FIG. 10 Lack of effect of $MNA^+$ on latex-induced activation of neutrophils

FIG. 2 shows thrombolytic response in vivo induced by $MNA^+$, and FIG. 3 shows a concomitant increase in level of 6-keto-$PGF_{1\alpha}$ (stable $PGI_2$ metabolite) in blood. Nicotinamide, nicotinic acid (FIG. 4), trigonelline and 2-PYR (FIG. 5) did not display a significant thrombolytic activity. However, $MAP^+$ (30 mg/kg) and $MNAF^+$ (30 mg/kg) each of them induced a thrombolytic response (FIG. 6 and FIG. 8) that was comparable to that induced by 30 mg/kg of $MNA^+$. $MAP^+$—induced thrombolysis was associated with the release of $PGI_2$ (FIG. 7), similarly as in the case of $MNA^+$-induced thrombolysis. $MNA^+$ (30-300 mg/kg) did not cause hypotension. As shown on FIG. 9 and FIG. 10, $MNA^+$ did not inhibit collagen-induced aggregation of platelets and latex-induced activation of neutrophils. The former response depends on $COX1-TXA_2$ and was abrogated by aspirin, whereas the latter one depends on NADPH oxidase and was abrogated by DPI or apocynin.

EXAMPLE 2

An Ant-Athrogenic Effect In Vivo in Patients

The anti-atherogenic effect of $MNA^+$ was investigated in 15 dyslipidemic patients.

The enrollment criteria were: high level of TG (≥250 mg/dl) and low level of HDL (≤35 mg/dl for male, ≤45 mg/dl for female). The mean age of the patients was 61.4 (range 45-81 years).

The patients were treated with $MNA^+$ for 2 weeks. The $MNA^+$ was administered orally, three times a day, one capsule (30 mg $MNA^+$) after meal.

The plasma levels of TC, TG, HDL were measured at baseline and after 2 weeks of therapy. The level of LDL was measured in those cases, where it was possible (due to high TG level).

It has been found that MNA+ reduced the TC (267.0 vs. 225.1 mg/dl) (−15.7%) and TG (472.6 vs 249.9 mg/dl) (−47.1%) levels between the baseline and 2 weeks measurements. The increase of the HDL (39.2 vs. 53.4 mg/dl) (36.2%) level was also observed after 2 weeks therapy. The significant reduction of TG/HDL ratio (13.9 vs. 5.8) was observed.

The invention claimed is:

1. A method for treatment of a disease caused by dysfunction of vascular endothelium, oxidative stress, or insufficient production of endothelial prostacyclin in a subject in need thereof, said method comprises administering to said subject an effective amount of a quaternary pyridinium salt of formula I:

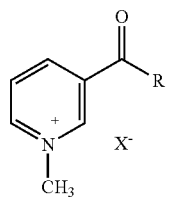

wherein R is $NH_2$, $CH_3$ or $N(H)CH_2OH$, and X is a pharmaceutically acceptable counterion, wherein said disease is selected from the group consisting of: chronic heart failure, pulmonary hypertension, diabetic retinopathy, diabetic nephropathy, nephrotic syndrome, chronic renal failure, adults respiratory distress syndrome (ARDS), cystic fibrosis, chronic obstructive pulmonary disease (COPD), preeclampsia, eclampsia, erectile dysfunction, Stein-Leventhal syndrome, sleep apnea, systemic lupus erythematosus, sickle cell anemia, non-specific inflammatory bowel diseases, gastric ulcers, duodenal ulcers, glaucoma, chronic liver diseases, primary amyloidosis, vascular dementia, Alzheimer's disease and Parkinson's disease.

2. The method of claim 1, wherein said disease is duodenal ulcer.

3. The method of claim 1, wherein said disease is chronic obstructive pulmonary disease (COPD).

4. The method of claim 1, wherein said quaternary pyridinium salt is administered orally.

5. The method of claim 1, wherein said quaternary pyridinium salt is administered via the inhalation route.

6. The method of claim 1, wherein said quaternary pyridinium salt is administered parenterally.

7. The method of claim 1, wherein said quaternary pyridinium salt is administered in the form of a composition with a pharmaceutically acceptable carrier.

8. The method of claim 1, wherein said subject has an insufficient production of endothelial prostacyclin.

9. The method of claim 1, wherein said quaternary pyridinium salt is a 1-methylnicotinamide chloride.

10. The method of claim 1, wherein X is a counterion acceptable for consumption.

11. The method of claim 10, wherein said quaternary pyridinium salt is in the form of a nutritional preparation or an oral dietary supplement.

12. The method of claim 11, wherein said nutritional preparation or said oral dietary supplement contains at least 5% by weight of said quaternary pyridinium salt.

13. The method of claim 10, wherein from about 10 mg to about 1000 mg of said quaternary pyridinium salt is administered daily, in single or divided doses.

14. The method of claim 2, wherein from about 10 mg to about 1000 mg of said quaternary pyridinium salt is administered daily, in single or divided doses.

15. The method of claim 3, wherein from about 10 mg to about 1000 mg of said quaternary pyridinium salt is administered daily, in single or divided doses.

* * * * *